(12) United States Patent
Pedain et al.

(10) Patent No.: US 7,266,227 B2
(45) Date of Patent: Sep. 4, 2007

(54) DEVICE AND METHOD FOR ADMINISTERING A SUBSTANCE

(75) Inventors: Christoph Pedain, München (DE); Philipp Tanner, München (DE); Andrea Hartlep, München (DE)

(73) Assignee: BrainLAB AG, Feldkirchen (DE)

( * ) Notice: Subject to any disclaimer, the term of this patent is extended or adjusted under 35 U.S.C. 154(b) by 822 days.

(21) Appl. No.: 10/075,108

(22) Filed: Feb. 13, 2002

(65) Prior Publication Data

US 2003/0114751 A1   Jun. 19, 2003

(30) Foreign Application Priority Data

Nov. 30, 2001 (EP) .................................. 01128614

(51) Int. Cl.
*G06K 9/00* (2006.01)

(52) U.S. Cl. .................................................. 382/128

(58) Field of Classification Search ........ 382/128–134; 600/431; 128/922
See application file for complete search history.

(56) References Cited

U.S. PATENT DOCUMENTS

| | | | |
|---|---|---|---|
| 5,919,135 A | 7/1999 | Lemelson | |
| 6,026,316 A * | 2/2000 | Kucharczyk et al. | 600/420 |
| 6,293,282 B1 | 9/2001 | Lemelson | |
| 6,549,803 B1 * | 4/2003 | Raghavan et al. | 600/431 |
| 2002/0168618 A1 * | 11/2002 | Anderson et al. | 434/262 |

FOREIGN PATENT DOCUMENTS

| | | | |
|---|---|---|---|
| WO | WO9628800 A1 * | 9/1996 | |
| WO | 01 85230 A | 11/2001 | |

* cited by examiner

*Primary Examiner*—Matthew C. Bella
*Assistant Examiner*—Patrick Edwards
(74) *Attorney, Agent, or Firm*—Renner, Otto, Boisselle and Sklar, LLP

(57) ABSTRACT

The present invention relates to: a method for planning an infusion, wherein patient data are captured and the infusion to be carried out is planned using the captured patient data; and to a computer program which may be loaded in the memory of a computer and which includes sections of software code with which the method is performed when the program is running on a computer; and to a device for planning an infusion, comprising a patient data capturing system and a computer system for carrying out planning based on the captured patient data; to a method for carrying out an infusion, wherein the infusion is planned and then carried out; and to a device for carrying out an infusion, comprising a verification device for comparing planned infusion data with actual infusion data.

19 Claims, 3 Drawing Sheets

DEVICE AND METHOD FOR ADMINISTERING A SUBSTANCE

FIELD OF THE INVENTION

Figure 1:
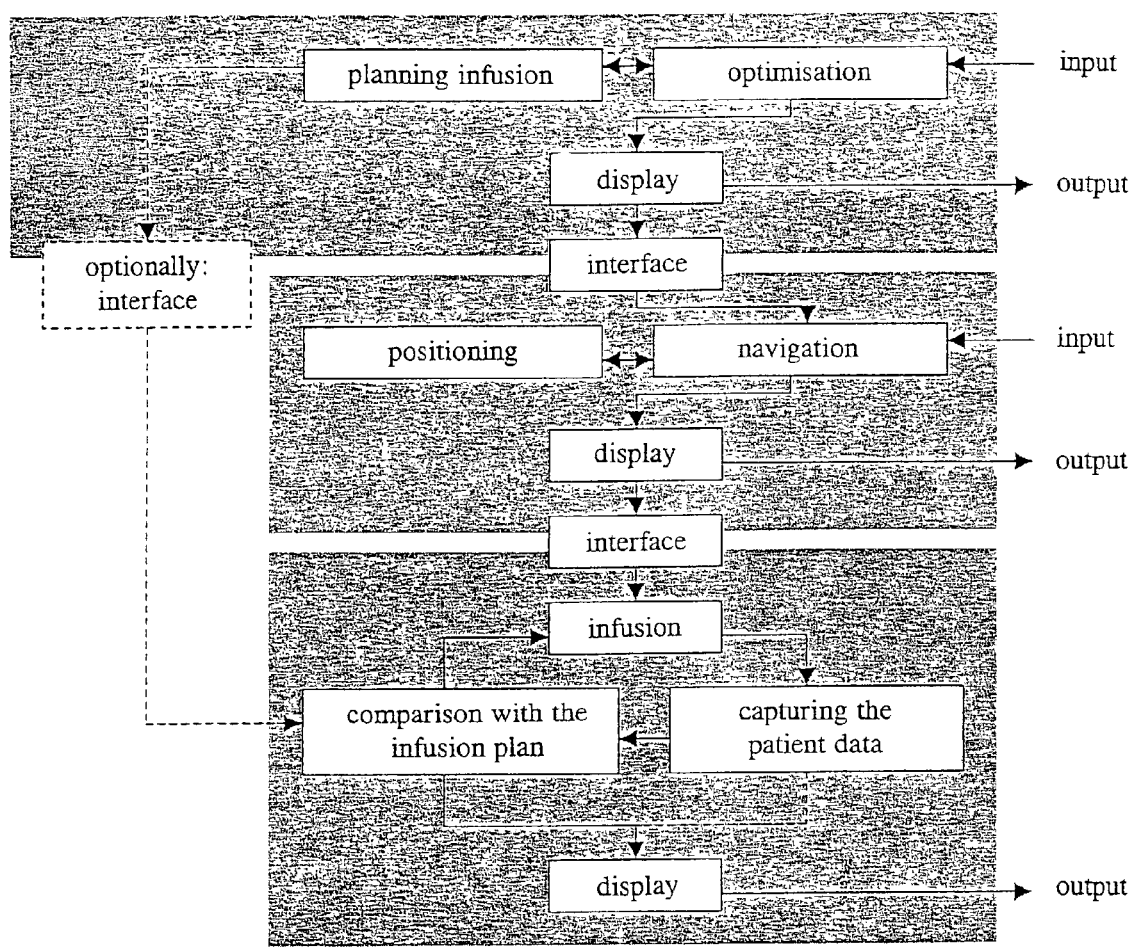

The present invention relates to methods, devices and computer programs which are used for preparing, planning, and carrying out an infusion.

BACKGROUND OF THE INVENTION

In general, the term "infusion" is to be understood in accordance with the invention as any administering of a for example liquid or solid substance and/or an infusing medium such as for example medicines, cells, genes, enzymes, proteins, antibodies, hormones, viruses or the like, said substance being introduced directly into a body and/or into body tissues, in order for example to surmount the blood-brain barrier. The substance can be delivered within a relatively short period of time, for example through an injection, or over a longer period of time, for example at a continuous and possibly variable rate of delivery of the substance.

Pharmaceutical substances have previously been administered by injecting a substance through the skin, directly into the vascular system, muscle tissue or subcutaneous tissue, or by positioning a catheter such that a substance could be introduced from without directly into body tissues. This depended crucially on the experience of the person who for example positioned the syringe so as to be able to position the substance to be administered as precisely as possible in the desired area of tissue. Due to inaccuracies and lack of knowledge of the substance-specific and patient-specific spreading mechanisms and distribution mechanisms in the corresponding tissue, as well as due to patient-specific variations in the arrangement of the tissue, for example in the case of a diseased tissue, it has been necessary to set a dosage required to treat a particular target tissue relatively high, in order to ensure that the substance delivered can reach the target tissue in a sufficient dosage, even when, due to inaccuracies, the location of injection of the substance does not lie directly in the target tissue. However, such substances, for example for treating tumors, are often toxic and thus unnecessarily debilitate surrounding tissue. If for example a tumor is to be treated using chemotherapy, toxic substances are used which can also damage healthy tissue.

On the other hand, it must be ensured, when performing an infusion, that the infusion locations and infusion parameters enable the infusion target area to be completely treated.

Various methods and devices have already been proposed, for enabling a substance to be introduced into a particular area of tissue in the first place, or for developing this to be more efficient, for example for treating tumors, Parkinson's disease or other illnesses.

It is known from US RE 37,410 E to inject a substance to be administered into a biodegradable material and to arrange the latter within or closely adjacent to a tumor to be treated, in order for example to surmount the blood-brain barrier in the case of a brain tumor. Once the bio-degradable material has degraded, the substance contained in it is released. This method, however, is relatively imprecise with respect to an individual, patient-specific dosage and also cannot be used for a protracted, specific treatment in which the treatment parameters may be altered.

A method for performing micro-infusions is known from U.S. Pat. No. 5,720,720, in which the tip of an infusion catheter is arranged inside a tissue structure. An active agent is delivered through the catheter, wherein a pressure gradient at the tip of the catheter is kept constant during infusion. This is to ensure a better distribution of the active agent, which would not be achievable by fusion alone.

U.S. Pat. No. 6,026,316 describes a method for delivering medicines, using data obtained from magnetic resonance or nuclear spin resonance (MR) to determine the position of the delivery device and to monitor the spatial distribution of the delivered medicine.

SUMMARY OF THE INVENTION

It is an object of the present invention to propose methods, devices and software using which a substance to be administered and/or an active agent can be introduced into a defined area of tissue in a patient-specific dosage.

This object is solved by the subjects of the independent claims. Advantageous embodiments follow from the sub-claims.

In accordance with a first aspect, the invention relates to a method for planning an infusion, i.e., for administering a substance or an active agent, in particular for injection into tissue, preferably into a predetermined tissue structure or tissue volume, wherein patient data or patient parameters obtained from them are captured. Known magnetic resonance or nuclear spin resonance methods (MRI), computer tomography (CT) methods, x-ray methods, ultrasound methods or other suitable methods, which enable the spatial structure of a body, in particular of a tissue structure, to be detected and displayed and/or functional data, such as for example patient-specific diffusion and perfusion properties, to be obtained, can be used in this respect. Infusion is planned in accordance with the invention using the patient data determined, i.e., for example the catheter to be used is suitably selected, the catheter is positioned with respect to the insertion location and depth of penetration, the infusing medium is selected and if necessary modified, for example thinned, and the pressure gradient over time with which the infusing medium is to be delivered through the catheter is predetermined, by taking into account various selectable preset figures, such as for example patient data or also parameters of available substances to be administered, parameters of the catheters which may be used and possibly of a pump which may be used. The aim of this selecting and setting is to inject a defined quantity of the substance to be administered into a target tissue volume, in order to obtain a particular concentration there, wherein as little of the substance to be administered as possible is to be introduced into non-target tissue.

The patent data captured may be used to position the infusion device(s), for example one or more catheters, wherein it is determined from these patient data where exactly in the patient's body a tissue volume to be treated, for example brain tumor, is situated. Using this information, a suitable catheter can be selected, for example from an available data base, by an operator or fully automatically, and possibly modified by post-processing, for example trimming the length of the catheter, in accordance with application or patient specifications, for example with respect to the desired depth of penetration into the tissue. Furthermore, it can be determined where a suitable point for inserting the catheter is, in order that the infusion debilitates as little healthy tissue as possible.

Known positioning methods can advantageously be used, for example using reflecting markers which are attached to the catheter and detected by IR cameras, in order to attach the catheter at a desired position on the patient. To this end, markers may also be attached to the patient himself/herself, which serve as a reference and through which a patient co-ordinate system is determined in which the catheter is placed at a particular, determined point.

Patient-specific parameters are preferably determined using the captured patient data for planning the infusion, for example the tissue or body structure in the area of the tissue to be treated by the infusion. It is particularly advantageous to determine the tissue density, the distribution of particular tissue structures, or the blood flow through a particular area of tissue, as patient parameters. Patient parameters may be obtained both directly from the captured patient data as well as from data bases or from a combination of values stored in data bases together with the captured patient data. Thus, values which may be used as patient parameters for planning an infusion can be stored, for example values in data bases relating to usual blood flow through particular areas of tissue, the diffusion and perfusion behavior of selected substances in the tissue under consideration, values relating to tissue behavior after a known substance has been delivered, for example swelling of the tissue or metabolic reactions.

It is furthermore advantageous to determine parameters of the infusing medium which characterize the substance to be administered or an active agent and, for example, define the physical, chemical and/or biological properties. Thus, information relating to the molecular or particle size of the substance to be administered, the rate of diffusion of this substance in a particular type of tissue, the metabolism and/or interaction of the substance with tissue due to metabolic processes, a diffusion coefficient known for the substance for the type of tissue to be treated or advantageous injection pressure or pressure gradient, an advantageous concentration, quantity or rate of delivery, whose magnitude of size is usually in the range ml/h, can be obtained from a data base. The parameters of the infusing medium listed by way of example can be used individually or in combination with other parameters for planning the infusion.

Advantageously, catheter variables are used, i.e., variables specific to a catheter for planning the infusion, wherein various types of a catheter could be provided to choose from, for example in a data base. Catheter parameters relevant to the infusion can be for example, the inner diameter of the catheter, surface finish, the material, in particular the rigidity of the catheter, the number and arrangement of outlets on the catheter or a known suitability of a particular type of catheter for a particular substance to be administered or a particular type of tissue or diseased tissue to be treated. In general, a number of catheters may also be used in accordance with the invention.

In accordance with the invention, a medicine, a solution containing cells, viruses, genes, enzymes, proteins, hormones, antibodies or a combination of these can be used as the infusing medium.

By using the patient parameters, parameters of the infusing medium and/or catheter parameters cited above by way of example, individually or in combination, together with the captured patient data, an infusion to be performed can be planned in accordance with the invention, such that as large a proportion of a substance as possible is introduced into a target area of tissue by infusion, wherein as little of the substance as possible is released into non-target tissue. Thus, in accordance with the invention, a substance to be introduced into a tissue by infusion can be introduced into an area of tissue to be treated in the patient using a particularly suitable and correctly positioned type of catheter and the correct injection pressure, at a suitable concentration and at a desired rate, taking into account metabolic and diffusion processes, in order to obtain a desired concentration of the substance to be introduced in said area of tissue, wherein—for example in the case of brain tumors—the blood-brain barrier may be surmounted by directly injecting the substance by infusion. Surrounding tissue is thus debilitated as little as possible.

In order to pre-plan the infusion, a simulation of the infusion to be performed can advantageously be performed in accordance with the invention, for example by calculating the distribution of infusing medium in the tissue using the captured patient data and the various parameters mentioned above. Using such a simulation, the distribution of infusing medium can be determined both statistically and dynamically as a function of time, and advantageously displayed graphically. In this way, it can be established even before performing an infusion whether a desired concentration distribution of the substance to be introduced in the target tissue can be obtained, or whether parameters of the infusing medium, catheter parameters or position parameters possibly have to be altered, to ensure a more successful infusion.

Furthermore, retro- or inverse planning can also be performed in accordance with the invention, wherein for example treatment data defined by an operator are preset, such as for example the target volume to be treated, advantageously together with high-risk structures such as for example nerve tracts which should not be compromised by the infusion, and details of the type of tissue to be treated. In this way, either fully automatically or by interaction with the operator, for example by displaying a selection menu, the course of the infusion can be established, i.e., one or more types of a catheter can be selected together with suitable infusing media, the arrangement(s) of catheters can be determined with respect to position and/or depth of penetration and the parameters of the infusing medium can be set, in order to enable a maximally optimal infusion treatment for the given target volume.

The planning methods described above, in particular the selecting of individual parameters, can be performed: fully automatically, for example using values stored in data bases; semi-automatically, for example by selections—still to be made by an operator—from a displayed menu; or manually, for example through parameter values inputted by an operator. In this respect, suitable computers are advantageously used, together with input and output elements, for example display elements displaying elements to be selected, tissue structures, calculated concentration distributions of the infusing medium and other information.

In accordance with another aspect, the present invention relates to a computer program which, when loaded or running on a computer, performs the method described above or parts of it. Equally, the present invention relates to a storage medium for such a program or to a computer program product comprising the aforementioned program.

A device in accordance with the invention, for planning an infusion, comprises a planning system consisting of a computer system, preferably having input and output devices and corresponding software. In this respect, a monitor is advantageously provided for displaying elements preset by the computer from data bases or values determined from calculations or spatial distributions.

A navigation system is also advantageously provided, consisting for example of reflecting markers, LEDs or coils attached to elements to be positioned and IR cameras or magnetic field generators, with which a catheter on a body, for example, can be positioned using a suitable, known software and hardware.

Generally, the device in accordance with the invention includes elements, devices and systems with which the steps of the method described above may be performed.

In accordance with another aspect, the invention relates to an infusion method, wherein infusion is preferably prepared as described above and the infusing medium is then introduced into the body or tissue.

Advantageously, a verification is performed continuously or at particular intervals in time during the infusion, the distribution of the infusing medium in the tissue during or after the infusion process being determined using a suitable data capture or representation system. Magnetic resonance, or nuclear spin resonance, or ultrasound methods, for example, may be used in this respect, wherein it may be advantageous to add a contrast medium to the infusing medium in order to be able to establish or measure the distribution of the infusing medium in the body tissue clearly.

Preferably, deviations between the actual distribution of the infusing medium in the tissue determined in the verification process and the planning data determined before or during the infusion are determined and preferably displayed. Advantageously, the infusion parameters are corrected, i.e., the chemical and/or physical composition and/or properties of the infusing medium is/are changed and/or the delivery is changed, for example the injection pressure or quantity delivered is changed, in order to be able to correct the deviation, determined during verification, from the planned distribution. If necessary, a catheter can also be repositioned or exchanged.

Advantageously, the deviation is verified and determined and the correction made in real time, such that the infusion can be performed regulated via a back-coupling, to obtain the desired successful infusion, i.e., to deliver the infusing medium to the given target area as desired.

In accordance with a further aspect, the present invention relates to a computer program which, when loaded or when running on a computer, performs the method described above. Equally, the present invention relates to a storage medium for such a program or to a computer program product comprising the aforementioned program.

According to a further aspect, the present invention relates to a device for carrying out an infusion method as described above, comprising a verification device for determining the spatial distribution of an infusing medium in a body, in particular in an area of tissue. The verification device can for example be a magnetic resonance or nuclear spin resonance, x-ray, or ultrasound system with which the infusing medium or its distribution and concentration in the tissue can be detected.

Advantageously, a computer system is preferably provided with a display device, to evaluate the determined spatial distribution of the infusing medium in the tissue, establish a deviation from a previously established infusion plan and possibly to automatically alter the infusion parameters or propose such a change to an operator, in order to modify the infusion such that it can be carried out as planned. To this end, systems can for example be provided using which the concentration of the infusing medium can be changed and/or the injection pressure or injection quantity can for example be altered by means of a pump, to obtain a distribution of the infusing medium in the tissue as previously planned. When a deviation from a given infusion plan is established during verification, the manner and magnitude of the change to the infusion parameters are advantageously determined using known action and function mechanisms. For example, the rate of delivery or the injection pressure is reduced when it is established that the infusing medium is spreading faster than predicted or is not being degraded by metabolic processes as quickly as expected.

DETAILED DESCRIPTION

The invention will now be described by way of preferred example embodiments.

Figure 2:
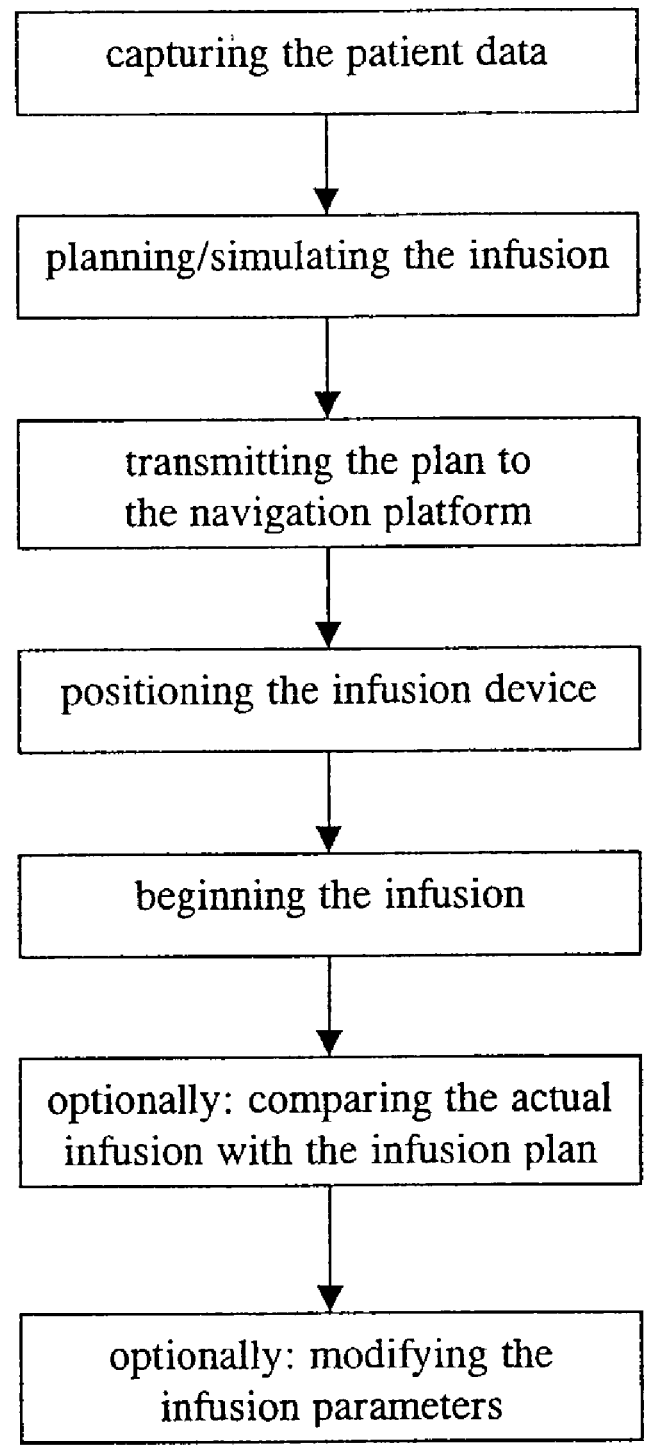
Figure 3:
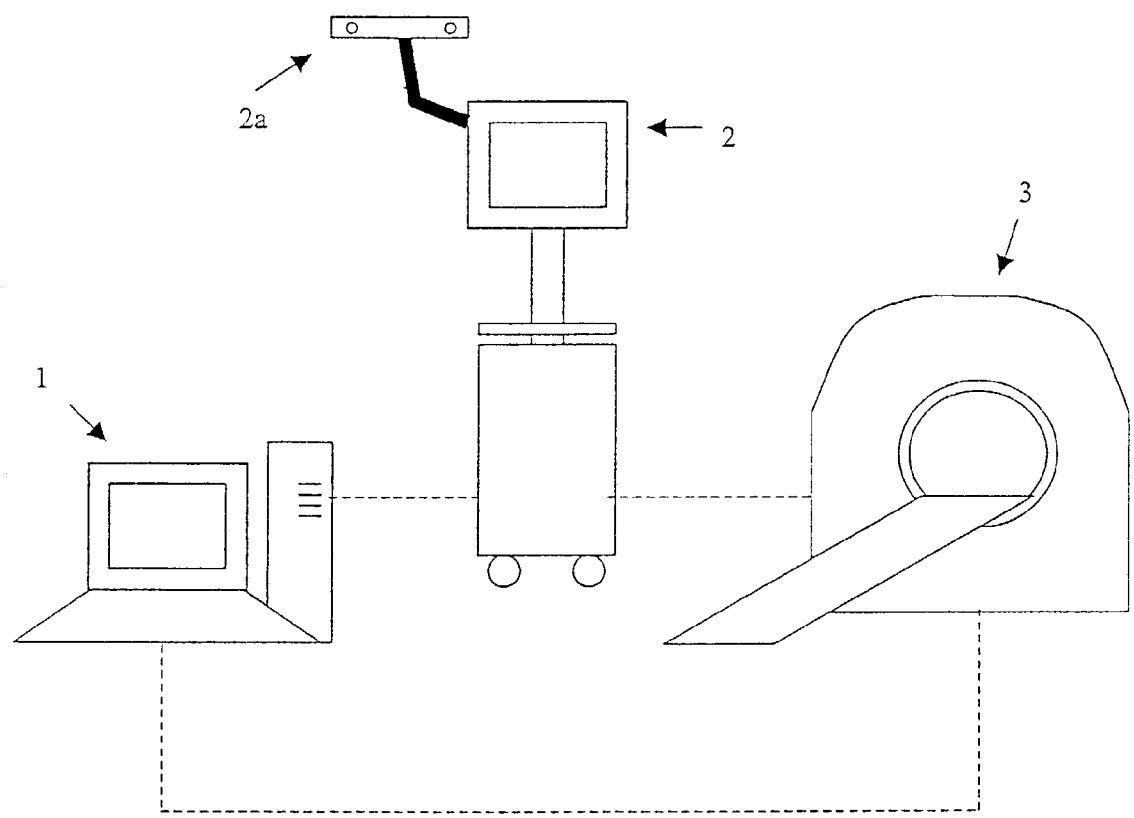

There is shown:

FIG. 1 a schematic diagram of a method for planning and carrying out an infusion;

FIG. 2 a simplified flow diagram of an infusion performed in accordance with the invention; and FIG. 3 a device which may be used when planning and carrying out an infusion.

FIG. 1 shows a schematic flow diagram for preparing and carrying out an infusion in accordance with the invention. As shown in FIG. 1, patient data are inputted, for example from a magnetic resonance or nuclear spin tomograph, which are used to determine a particular target area of tissue for the infusion and to plan the infusion dosage to be delivered. These data can be obtained for example through the magnetic resonance or nuclear spin resonance system 3 as shown schematically in FIG. 3, after a patient to be treated has been examined.

Using parameters for the properties of the tissue structures and for various types of catheter, stored for example in data bases, one or more catheters suitable for the infusion can be selected, once the exact location of the tissue volume to be treated has been determined. The patient parameters obtained, for example by the magnetic resonance or nuclear spin resonance method, can be used together with the catheter parameters and the parameters of the infusing medium, also for example stored in data bases, to plan the infusion. The corresponding parameters can thus be optimized, on the ancillary condition that an large as possible proportion of the infusing medium is introduced into the target tissue at the desired concentration, wherein as little of the infusing medium as possible is to reach tissue lying outside the target tissue. In general, as few catheters or needles should be placed as possible, said catheters or needles being fed through as few access ports as possible. This optimized planning of the infusion dosage is to be outputted via a display, such that for example a two-dimensional or three-dimensional representation can be outputted through representations of various incision planes, in order to display the results of infusion planning.

The infusion plan produced in this way is communicated via an interface to a navigation system, such as for example the VectorVision® system shown schematically in FIG. 3, in order to position the selected catheter or catheters at the given points on the body, based on the planning data. The catheter(s) can be positioned automatically, for example using a robot, or by hand guided by the navigation system, a display device showing whether a catheter a correctly positioned or still has to be moved in a particular direction.

Once the catheter(s) has/have been successfully positioned, the actual infusion is carried out using the parameters of the infusing medium set by the planning. To this end, patient data are again captured, to determine the actual distribution of infusing medium in the tissue. Using the parameters set by the planning, and the results of the simulation of the infusion based on them, a comparison is made between the actual distribution of the infusing medium and the predicted, desired distribution of the infusing medium, and the parameters—for example the concentration of injecting medium, the quantity delivered or the injection pressure for carrying out the infusion—are altered as appropriate, preferably taking into account known action mechanisms in order to obtain the desired, planned result of infusion. The measured, actual distribution of the infusing medium concentration, preferably together with possible deviations and correcting methods, can again be outputted via a display, in order for example to enable an operator to manually intercede in the injection method.

FIG. 2 schematically shows a simplified sequence of planning and carrying out an injection in accordance with the invention. Firstly, patient data are captured using an imaging diagnostic method such as for example a magnetic resonance or nuclear spin resonance method, to obtain the current patient parameters such as for example tissue density, blood flow, and the location of a tissue to be treated. Using the patient parameters determined in this way, and with catheter parameters and parameters of the infusing medium obtained from a data base and/or pre-set for a particular infusion, the infusion is planned and/or simulated. Based on the parameter data determined in this way, the infusion plan is forwarded to a navigation platform, using which the catheter or catheters are to be positioned on the patient as provided for in the infusion plan. Infusion begins once the infusion device has been positioned and is carried out using the planned and possibly simulated parameters, wherein—as shown in FIGS. 1 and 2—the infusion actually performed is optionally compared with the infusion plan, and in the event of deviations, the corresponding parameters are modified, preferably using known action mechanisms.

FIG. 3 schematically shows a device which may be used when planning and carrying out an infusion in accordance with the invention. Patient data are obtained in a magnetic resonance or nuclear spin tomograph 3 and forwarded to a planning system 1 and to a navigation system 2. The catheter or catheters are positioned at a desired point on a body by the navigation system 2, using for example known reflectors or markers, attached to one or more catheters, positional data of the markers being captured by IR cameras 2a. In order to carry out the infusion, the planning system 1 determines the suitable catheter parameters and parameters of the infusing medium for a pre-set infusion to be carried out, using patient parameters determined by the magnetic resonance or nuclear spin resonance system 3.

The invention claimed is:

1. A method for planning administration of a substance into a patient, comprising the steps of:
   capturing patient data;
   prior to positioning an infusion catheter in a body of the patient, using said patient data to plan an infusion of the substance into the patient;
   performing a simulation of the planned infusion to obtain simulation data corresponding to a distribution of the substance within the patient;
   determining from the simulation data if a desired infusion plan for administration of the substance into the patient can be obtained; and
   if the determining step determines a desired substance distribution can be obtained, using a navigation system to position the infusion catheter in the body of the patient as specified by the infusion plan.

2. The method as set forth in claim 1, wherein said infusion catheter is positioned on the patient with respect to the infusion location and/or to the depth of penetration as set forth in the plan.

3. The method as set forth in claim 1, wherein said patient data are captured by a magnetic resonance method (MRI), a computer tomography method (CT), an x-ray method or an ultrasound method.

4. The method as set forth in claim 1, wherein patient parameters are obtained from said captured patient data and are used for planning said infusion.

5. The method as set forth in claim 4, wherein information on the tissue structure, tissue density, blood flow and/or metabolic properties of said tissue is used as said patient parameters.

6. The method as set forth in claim 1, wherein parameters of said substance, defining chemical, biological and/or physical properties of said substance, are used for planning said infusion.

7. The method as set forth in claim 1, wherein catheter parameters are used for planning said infusion.

8. The method as set forth in claim 1, wherein the distribution of said substance is simulated based on patient parameters obtained from said captured patient data, catheter parameters and parameters of said substance.

9. The method as set forth in claim 1, wherein a target volume and/or a distribution of the substance in the patient is pre-set, and catheter parameters and parameters of said substance are based on the preset target volume and preset distribution.

10. A computer program embodied on a computer readable medium which may be loaded in the memory of a computer, and includes sections of software code with which the steps in accordance with claim 1 may be performed when said program is running on a computer.

11. The method as set forth in claim 1, further comprising: comparing the simulation to a desired result; and adjusting the plan based on the comparison.

12. The method as set forth in claim 11, wherein comparing includes comparing at least one of a desired concentration of the substance in a target tissue volume relative to a simulated concentration of the substance in the target tissue volume, or a desired concentration of the substance in a non-target tissue volume relative to a simulated concentration of the substance in the non-target tissue volume.

13. A device for planning administration of a substance into a patient, comprising:
   a computer system configured to use patient data captured from a patient data capturing system to plan, prior to positioning an infusion catheter in a body of the patient, an infusion of the substance into the patient based on the patient data catheter parameters and/or parameters of the substance, and to simulate the planned infusion to obtain simulation data corresponding to a distribution of the substance within the patient, wherein the simulation data is used to determine if a desired infusion plan can be obtained for maximizing the quantity of the substance administered to a target tissue volume of the patient while minimizing the delivery of the substance to non-target tissue; and
   a navigation system for positioning the infusion catheter based on said desired plan.

14. A method for carrying out an infusion, comprising the steps of:
   planning said infusion prior to positioning an infusion catheter in a body of a patient;
   performing a simulation of the planned infusion to obtain simulation data corresponding to a distribution of the substance within the patient;
   determining from the simulation data if a defined quantity of the substance is administered to a target tissue volume of the patient while minimizing the delivery of the substance to non-target tissue;

if the determining step indicates an acceptable result, using a navigation system to position the infusion catheter in the body of the patient as specified by the planned infusion; and executing the planned infusion.

15. The infusion method as set forth in claim 14, wherein said infusion is planned in accordance with a method wherein patient data are captured and the infusion to be carried out is planned using said patient data.

16. The method as set forth in claim 14, wherein actual infusion data are compared with the planned infusion data.

17. The method as set forth in claim 16, wherein deviations between said planned infusion data and said actual infusion data are determined.

18. The method as set forth in claim 17, wherein the infusion parameters are corrected based on said determined deviations.

19. A computer program embodied on a computer readable medium which may be loaded in the memory of a computer, and includes sections of software code with which the steps in accordance with claim 14 may be performed when said program is running on a computer.

* * * * *